(12) United States Patent
Hardahl et al.

(10) Patent No.: US 7,477,936 B2
(45) Date of Patent: Jan. 13, 2009

(54) SYSTEM AND A METHOD FOR ANALYZING ECG CURVATURE

(75) Inventors: Thomas Bork Hardahl, Aalborg (DK);
Claus Graff, Klarup (DK); Mads Peter Andersen, Aalborg Ø (DK); Egon Toft, Aalborg Ø (DK); Johannes Jan Struijk, Aalborg Ø (DK); Jørgen Kim Kanters, Ålsgårde (DK)

(73) Assignee: Aalborg Universitet, Aalborg Ø (DK)

( * ) Notice: Subject to any disclaimer, the term of this patent is extended or adjusted under 35 U.S.C. 154(b) by 229 days.

(21) Appl. No.: 11/014,915

(22) Filed: Dec. 20, 2004

(65) Prior Publication Data

US 2005/0177049 A1    Aug. 11, 2005

Related U.S. Application Data

(60) Provisional application No. 60/530,665, filed on Dec. 19, 2003.

(51) Int. Cl.
*A61B 5/0452*    (2006.01)

(52) U.S. Cl. .................. 600/509; 600/513; 600/516; 600/517

(58) Field of Classification Search .................. None
See application file for complete search history.

(56) References Cited

U.S. PATENT DOCUMENTS

| | | | |
|---|---|---|---|
| 5,419,338 A | 5/1995 | Sarma et al. | |
| 5,749,367 A | 5/1998 | Gamlyn et al. | |
| 5,803,084 A | 9/1998 | Olson | |
| 6,275,732 B1 * | 8/2001 | Hsu et al. | 607/14 |

(Continued)

FOREIGN PATENT DOCUMENTS

| | | |
|---|---|---|
| GB | 2387442 | 10/2003 |
| WO | WO 9119452 | 12/1991 |

OTHER PUBLICATIONS

Bailon et al.; *Coronary artery disease diagnosis based on exercise electrocardiogram indexes from repolarization, depolarization and heart rate variability*; Medical and Biological Engineering and Computing 2003; vol. 41; pp. 561-571.

Zhang et al.; *Spectrum of ST-T-Wave patterns and Repolarization Parameters in Congenital Long-QT Syndrome*; Circulation; Dec. 5, 2000; Amer. Heart Ass'n. pp. 2849-2855.

*Primary Examiner*—Carl H Layno
*Assistant Examiner*—Eugene T Wu
(74) *Attorney, Agent, or Firm*—James Creighton Wray; Clifford D. Hyra

(57) ABSTRACT

A system or a method for analysing ECG curvature wherein at least one among a number of different parameters is isolated, for indicating symptoms of diseases having influence on the ECG curvature. The system and method provides for objective, fast and effective indication of a number of symptoms derivable from an ECG curve which may be indicative of one or more diseases. This can be achieved when a first number of selected parameters are combined in at least a first mathematical analysis, where the result of the analysis can be represented as a point in a coordinate system comprising at least two axes where the system can compare the actual placement in the coordinate system with a number of reference parameters stored in the system for indicating diseases having influence on the ECG curvature.

16 Claims, 25 Drawing Sheets

U.S. PATENT DOCUMENTS 6,324,423 B1 11/2001 Callahan et al.
6,389,308 B1 5/2002 Shusterman
6,684,100 B1 * 1/2004 Sweeney et al. ............ 600/517
2002/0143263 A1 10/2002 Shusterman

* cited by examiner

Non ST-elevation myocardial infarction

- ST depression
- T-wave morphology
- Q-wave morphology

- P-wave morphology
- QRS duration
- S-wave morphology
- T-wave morphology

- PR-duration
- ST-elevation
- ST morphology
- T-wave morphology

Right bundle branch block RBBB

- QRS duration
- R-wave morphology
- T-wave morphology
- ST-elevation

Left bundle branch block LBBB

- QRS duration
- R-wave morphology
- T-wave morphology

- Q-T duration
- T-wave morphology

Changes in the ECG in lead II caused by hyperkalemia

- P-wave morphology
- T-wave morphology
- QRS duration
- QT duration
- PR duration Changes in the ECG in lead II caused by hypokalemia

- QT duration
- T-wave morphology
- ST depression

Pericarditis

- ST elevation
- ST morphology
- Q-wave morphology
- PR depression

Right Ventricular Hypertrophy (RVH)

- Q-wave morphology
- QRS duration
- S-wave morphology
- T-wave morphology

Left Ventricular Hypertrophy (LVH)

- Q-wave morphology
- QRS duration
- S-wave morphology
- T-wave morphology

Arrhythmogenic Right Ventricular Dysplasia

- QRS duration
- S-wave morphology
- T-wave morphology

SYSTEM AND A METHOD FOR ANALYZING ECG CURVATURE

This application claims the benefit of U.S. Provisional Application No. 60/530,665 filed Dec. 19, 2003.

BACKGROUND OF THE INVENTION

Field of the Invention

The present invention relates to a system for analysing ECG curvature where at least one among a number of different parameters is isolated, which system has a input means connected to an ECG source, where the different parameters of a received ECG curvature are indicated and/or isolated and for indicating possible symptoms which relates to or are indications of certain deceases, where said deceases are known to influence the ECG curvature.

The present invention further relates to a method for analysing ECG curvature, which curvature contains a number of parameters.

The aim of the invention is to achieve a system and a method for objective, fast and effective indication of a number of symptoms derivable from an ECG curve which may be indicative of one or more diseases.

SUMMARY OF THE INVENTION

This can be achieved with the system previously described if a first number of selected parameters, are combined in at least a first mathematical analysis, where the result of the analysis can be represented as a point in a coordinate system comprising at least two axes where the system can compare the actual placement in the coordinate system with a number of reference parameters stored in the system for indicating diseases having influence on the ECG curvature.

Hereby, it is achieved that any symptom of a disease having an indication (influence) in the ECG curvature can be detected in an objective, automated and very fast way. The system might be used under field conditions such as in ambulances or in other situations where a fast indication of heart diseases is needed in order to help the patient in a correct way as early as possible. The analysis that takes place in an ambulance on its way to the hospital, can by transmitting the results to the hospital, allow the doctor at the hospital to give feedback to the personnel in the ambulance so that the correct treatment of the patient may start. At the same time, the hospital can prepare the correct activity for the incoming patient. The system could be very important for ECG analyses for all non-specialists in the field if they have to analyse a ECG curvature.

The scope of the invention can also be fulfilled with a method for analysing the ECG curvature if the method incorporates the steps of:
  receiving ECG curvature from a source,
  indicating a number of different parameters contained in the received ECG curvature,
  storing the parameters in storage means,
  selecting disease specific parameters in the storage means
  combining selected parameters in mathematical analysing means
  representing the result of the mathematical analysis as a point in a coordinate system, comprising at least two axes,
  comparing the actual placement in the coordinate system with a number of reference parameters stored in a memory,
  indicating possible diseases having the determined influence on the ECG curvature.

In this way as already described, a very effective analysis of the ECG curvature is achieved.

In FIGS. 20a and 20b, the parameters are illustrated on a typical ECG curvature in order to illustrate the different curve sections isolated by the analysis, and referred to by parameters, intervals and complexes.

The heart generates an electrical signal ECG. The waves at the ECG-signal P,Q,R,S,T and U are due to depolarisation and repolarisation of the heart.

The QRS-complex contains the Q,R and S wave and goes from the Q-onset to S-offset.

The QT interval starts at the beginning of QRS (Q-onset) and ends at the T-wave onset.

The RR interval goes from one R-peak to the following.

The PR interval is from the beginning of P to the beginning of QRS (Q-onset).

QRS duration is the width the QRS complex.

The ST-segment starts at the QRS-complex offset and ends at the T-wave onset.

The analysing process is repeated in the system for further selected parameters in order to indicate further possible diseases or symptoms. Hereby, it is achieved that the system or the method can be repeated several times with different combinations of parameters. In order to analyse for a high number of possible diseases, each time a result of an analysis is achieved, the parameters are compared with stored parameters where every stored parameter is an indication of a symptom of a known disease. With the system, a deviation of parameters from the stored data indicating symptoms of an exact disease may also be interpreted for further reference. Parameters could be controlled, and if the storage means has an enormously high number of reference parameters relating to various symptoms, testing for all symptoms and correlated diseases having influence on the ECG curvature may be performed.

The system or method divides the parameters into at least two main groups, which groups contain parameters of symmetry, flatness and duration relating to the actual ECG curvature. In this way, it is achieved that the parameters are grouped in the system, and in every group, they can be further subdivided into a specific number of possible parameters. Keeping the number of parameters relatively small, the analysis takes place in a faster way.

The group of symmetry might contain at least the following parameters:
  S1 Skewness evaluated from Tstart to Tend,
  S2 Skewness evaluated from Tstart to Tend with Ttop as mean,
  S3 Skewness evaluated in a symmetric interval, 10% of the Tstart-Tend interval surrounding Ttop with Ttop as mean
  S4 Skewness evaluated in a symmetric interval, 20% of the Tstart-Tend interval surrounding Ttop wit Ttop as mean,
  S5 Ratio of the time interval from Tstart to Ttop and the time interval from Ttop to Tend.
  S6 Ratio of the average slope from Tstart to Ttop and from Ttop to Tend.

The group of flatness might contain at least the following parameters:
  F1 Kurtosis evaluated from Tstart to Tend,
  F2 F1 normalized by the absolute Rtop-Qnadir value,
  F3 Kurtosis evaluated from Tstart to Tend with Ttop as mean,
  F4 F3 normalized by absolute Rtop-Qnadir value, F5 Kurtosis evaluated in a symmetric interval, 10% of the Tstart-Tend interval surrounding Ttop with Ttop as mean, F6 F5 normalized by absolute Rtop-Qnadir value, F7 Kurtosis evaluated in a symmetric interval, 20% of the Tstart-Tend interval surrounding Ttop with Ttop as mean, F8 Kurtosis normalized by the value of Rtop with Ttop as mean, F9 Ratio of the total area under the T-wave from Tstart to Ttop and the corresponding time interval, F10 F9 normalized by absolute Rtop-Qnadir value, F11 Ratio of the total area under the T-wave from Ttop to Tend and the corresponding time interval, F12 F11 normalized by absolute Rtop-Qnadir value F13 Ratio of the total area under the T-wave from Tstart to Tend and the corresponding time interval, F14 F13 normalized by absolute Rtop-Qnadir value, F15 Ratio of the height of Rtop and the width of the Tstart-Tend interval.

The group of duration might contain at least the following parameters:

QTc The Q-T interval normalized by the square root of the R-R interval according to Bazett's formula, D2 Time interval from Tstart to Tend, D3 Time interval from Tstart to Ttop, D4 Time interval from Ttop to Tend.

The groups of parameters could contain further parameters and the group may contain a number of sub groups.

Combining parameters, the system and/or method may form the different groups. When combining parameters from different groups, a much better result is achieved than when only using parameters from the same group. The parameters can be an elevation of the curve; they can be the morphology of the curve; or they could be time-deviations as an example of possible parameters. When combining parameters, a precise analysis can take place because a specific combination of parameters can indicate a specific disease and it is possible effectively to select between ECG-signals that look very much alike, but which indicate different diseases.

The system and/or method can analyse the QT interval of the ECG curvature for indicating Long QT syndrome. This way, the Long QT syndrome can be indicated in an objective and effective manner which might occur with children right after they are born in order to start a treatment of Long QT syndrome as early as possible. The method can differentiate between different genotypes of the Long QT Syndrome, which is important for the treatment. Hereby can be achieved that the correct medical treatments can be started.

The system and/or method can analyse for ST-elevation myocardial infarction by analysing at least the following parameters: ST elevation, ST morphology, T wave morphology and Q wave morphology. In this way, a very effective indication for ST-elevation myocardial infarction is achieved at the correct activity can be stated as early as possible.

The system and/or method can analyse for Non ST-elevation myocardial infarction by analysing at least the following parameters: ST depression, T wave morphology and Q wave morphology. Non ST-elevation myocardial infarction can also be detected in a highly effective way and correct treatment can be stated.

The system and/or method can analyse for Cardiomyopathia by analysing at least the following parameters: P wave morphology, QRS duration, S Wave morphology, T wave morphology. Cardiomyopathia can in this way be effectively detected.

The system and/or method can analyse for Brugada Syndrome by analysing at least the following parameters: PR-duration, ST elevation, ST morphology and T wave morphology. Hereby, it is achieved that Brugada Syndrome is detected in a very effective and fast way.

The system and/or method can analyse for Right bundle branch block RBBB by analysing at least the following parameters: QRS duration, QRS morphology, T wave morphology and ST elevation. In this way, an indication of Right bundle branch block RBBB is achieved in an effective way.

The system and/or method can analyse for Left bundle branch block LBBB by analysing at least the following parameters: QRS duration, R wave morphology and T wave morphology. An effective indication of Left bundle branch block LBBB is also possible with this method or by using the system.

The system and/or method can analyse for Short QT Syndrome by analysing at least the following parameters: Q-T duration and T wave morphology. Short QT Syndrome can also be analysed effectively.

The system and/or method can analyse for Hyperkalemia by analysing at least the following parameters: P wave morphology, T wave morphology, QRS duration, QT duration and PR duration. Hereby, indication of Hyperkalemia is achieved in a highly effective way.

The system and/or method can analyse for Hypokalemia by analysing at least the following parameters: QT duration, T wave morphology and ST depression. Hereby, it is achieved that Hypokalemia is indicated effectively.

The system and/or method can analyse for peri/myocarditis by analysing at least the following parameters: ST elevation, ST morphology, Q wave morphology and PR depression. Hereby, it is achieved that peri/myocarditis is detected effectively.

The system and/or method can analyse for Right Ventricular Hypertrophy by analysing at least the following parameters: Q wave morphology, QRS duration, S wave morphology and T wave morphology. Herby, it is achieved that Right Ventricular Hypertrophy is indicated effectively.

The system and/or method can analyse for Left Ventricular Hypertrophy by analysing at least the following parameters: Q wave morphology, QRS duration, S wave morphology and T wave morphology. Also Left Venticular Hypertrophy can be detected effectively.

The system and/or method can analyse for Arrhythmogenic Right Ventricular Dysplasia by analysing at least the following parameters: QRS duration, S wave morphology and T wave morphology. Hereby, it is achieved that Arrhythmogenic Right Ventricular Dysplasia is detected in an effective way.

These and further and other objects and features of the invention are apparent in the disclosure, which includes the above and ongoing written specification, with the claims and the drawings.

DETAILED DESCRIPTION OF PREFERRED EMBODIMENTS

Figure 1:
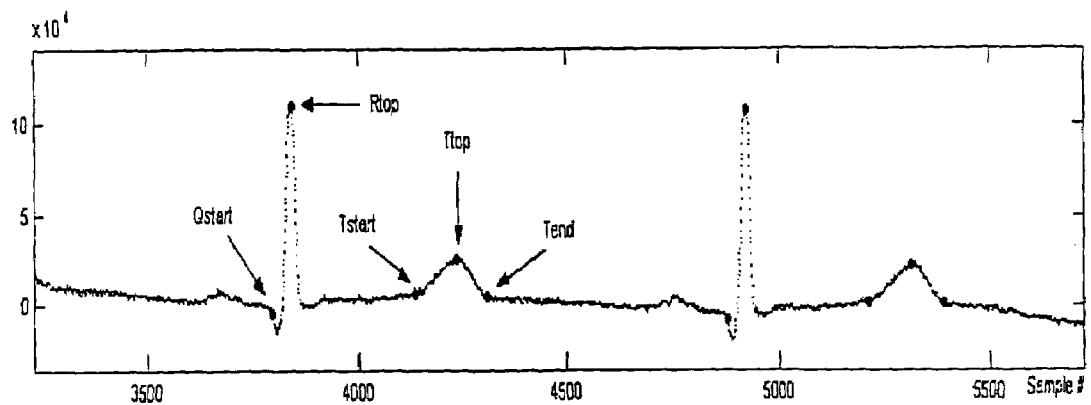
FIG. 1 shows an example of the result of the event detection algorithm.

Below is described one possible method and a system to illustrate the invention.

Abstract

The Long QT Syndrome is a genetic disorder characterized by abnormal cardiac repolarisation resulting in prolonged QT duration, syncopal episodes and increased risk of sudden cardiac death. Mutations in the KvLQT1—and HERG genes account for more than 90% of all LQTS patients. The QT interval duration is the only ECG-based quantifier of LQTS used in clinical practice today. However duration is only a gross estimate of repolarisation and does not allow perfect discrimination between KvLQT1, HERG and normal subjects. Studies have shown that T-wave morphology parameters are useful discriminators in LQTS, but no single parameter has proven to be sufficient. In this study we present a novel multivariate discrimination method based on a combination of T-wave symmetry-, flatness- and duration parameters. 16 subjects were included in the study—8 normal, 5 HERG and 3 KvLQT1 patients. Genotypes were known for all LQTS patients, but one. Standard 12—lead ECG's were recorded on each subject. An automatic ECG event detection algorithm was implemented. The signal was highpass filtered and normalized with respect to the isoelectric level to ensure a stable baseline. 4 parameters describing the duration of repolarisation, 6 symmetry-and 15 flatness parameters were calculated to characterize each of the T-waves.

The mean values of lead V5 and the interlead standard deviations were used as parameter values. Stepwise discriminant analysis was performed to obtain two discriminant functions based on the five strongest discriminatory parameters. The resulting discriminant functions include 2 duration-, 2 symmetry- and 1 flatness parameter. The two functions classify all subjects correctly (p>0.0001, p<0.005). Further discriminant analysis with a reduced number of parameter categories implied that superior classification is obtained when using all three parameter categories presented. A combination of parameters from the three categories symmetry, flatness and duration of repolarisation was sufficient to correctly classify ECG recordings from the KvLQT1, HERG and normal subjects in this study. This multivariate approach may prove to be a powerful clinical tool.

1. Introduction

The Long QT Syndrome (LQTS) represents a hereditary genetic disorder characterized by the presence of prolonged QT duration on the ECG, syncopal episodes due to polymorphic ventricular tachycardia (torsade de pointes), and arrythmogenic sudden cardiac death.

Mutations involving 6 different genes have been identified in LQTS subjects. These mutations result in structural and functional changes in ion-channel proteins and currents. The changes are manifest by QT prolongation and morphological gene-specific repolarisation patterns. The most prevalent genes affected in LQTS patients are KvLQT1 and HERG which account for more than 90% of LQTS genotype patients. The current study focuses on carriers of these two genes. Although some attempts have been made to develop quantitative measures that link different repolarisation abnormalities to specific LQTS related channel-opathies these methods have so far failed to provide a solid diagnostic yield. In current practice the duration of the QT interval is the only widely accepted quantifier of ventricular repolarisation. Yet, it has been recognized that the duration of the QT interval is only a gross estimate of repolarisation since T-wave morphology is also important when characterizing the QT interval. This is evidenced by the fact that approximately 10% of all mutation carriers have a normal Bazett corrected QTc (<440 ms) and 40% of KvLQT1 and HERG carriers show QTc values between 410-470 ms that overlap with non-carriers. Conversely only 2% of all carriers present with a normal ST-T pattern and a normal QT interval. Morphological aberrations thus carry major implications for the identification of abnormal repolarisation and have been included as diagnostic criteria equivalent to that of a positive family history for LQTS.

Studies have shown that affected KvLQT1 patients generally show broad based T-waves with a normal to relatively high amplitude and often without a distinct T-wave onset. For individuals with mutations involving the HERG gene the aforementioned studies have generally found low amplitude T-waves with bifid T-waves in 60% or more of the carriers.

Cardiologists already include a qualitative assessment of T-wave morphology from the ECG in order to obtain information that augments the clinically established QT interval measurement and facilitates discrimination between LQTS genotypes. However qualitative description of repolarisation morphology may be biased due to intra- and interpersonal variability thus indicating the need for a standardized quantitative measure of this parameter.

In the following is presented a novel multivariate categorization method that allows discrimination between KvLQT1, HERG and normal individuals based on Twave morphology recorded from 12-lead ECG's. Hallmark morphological features of T-waves reported in the literature for these three groups served as inspiration for selecting three primary T-wave characteristics to be assessed. These characteristics are symmetry, flatness and duration.

2. Methods 2.1 Subjects

The study included ECG recordings from 8 female and 8 male subjects. The subjects were divided into four groups; 3 KvLQT1 (aged 20-48, 2 females), 5 HERG (aged 13-76, 2 females), 8 normal (aged 23-31, 4 females). Genotypes were known for all KvLQT1 and HERG subjects with a single exception: 1 patient was categorized as a KvLQT1 subject by anamnesis and ECG-analysis. In the normal group there were no reports of prior cardiac diseases or LQTS family precedent.

2.2 Data Collection

Data acquisition was carried out with the subjects resting in supine position. The equipment used for data acquisition was a portable digital ECG recording system, "Cardio Perfect Resting ECG system" manufactured by Cardiocontrol. Recording was divided into three sessions. Data was collected from 8 leads (I-III, V2-V6) with a sampling rate of 1200 Hz. Signal recording length was 75 s. in the first session and 150 s. in the last two sessions.

Following data acquisition, SCP files generated by the Cardio perfect software were exported from a MSDE/SQL7 server and subsequently converted to .MAT files using SCP-Batch Converter.

2.3 Algorithm for Detection of Events in the ECG

To facilitate evaluation of the repolarisation process and the QT interval, several events in the ECG were detected (Qstart, Rtop, Tstart, Ttop and Tend). An algorithm for detecting these events was implemented in Matlab 6.0.

The method is based on prior work published by Laguna et al. and uses adaptive thresholding techniques applied to a digitally filtered and differentiated signal. A minor extension to the algorithm was incorporated to enable the detection of Tstart. Tstart was detected with a technique equivalent to the technique for detecting Tend. FIG. 1 shows an example of the result of the event detection algorithm.

FIG. 1. Important events that are used to describe repolarisation are marked by dots by the event detection algorithm. The algorithm is able to detect the events on all 8 recorded leads.

2.4 Preliminary Signal Processing

Figure 2:
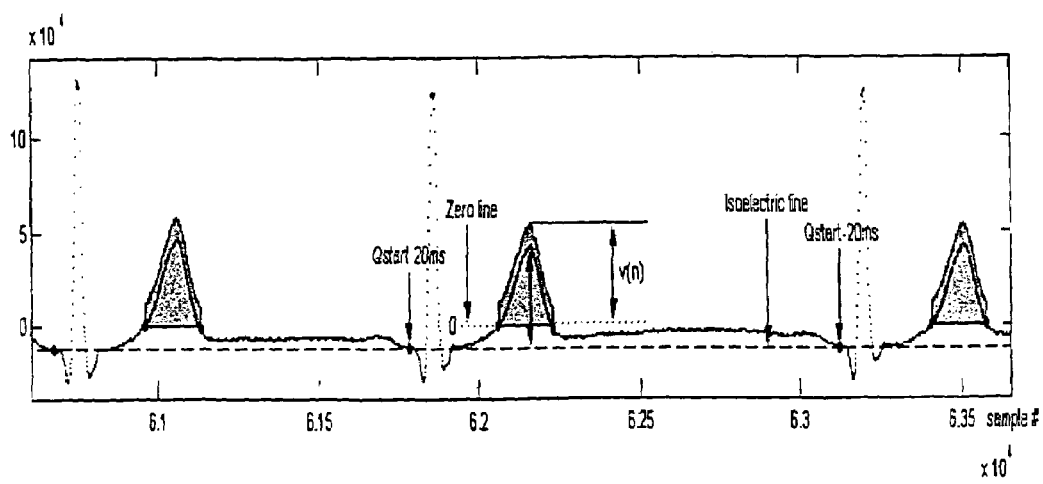
FIG. 2 shows preliminary signal processing.

Evaluation of the QT interval and the repolarisation process was done on the basis of an ECG signal with stabilized baseline. This was achieved through preliminary signal processing. The "raw" ECG was filtered by a minimum order equiripple high pass filter with a cut-off frequency of 2 Hz, 60 dB damping in 0 Hz and 1 dB ripple in the passband (N=1276). After filtering, the signal had an almost stable baseline. In order to improve stability, isoelectric lines in the signal were estimated from one P-Q interval (Qstart minus 20 ms) to the following P-Q interval (Qstart minus 20 ms). The signal was then normalized by subtracting the line value from the corresponding signal values. This process is shown in FIG. 2.

2.5 T-Wave Morphology Parameters

In order to characterize the T-wave morphology, a number of parameters were selected. The parameters were chosen to cover each of the three categories: Twave symmetry, T-wave flatness and duration. The parameters are listed and described in table 1.

Figure 3A:
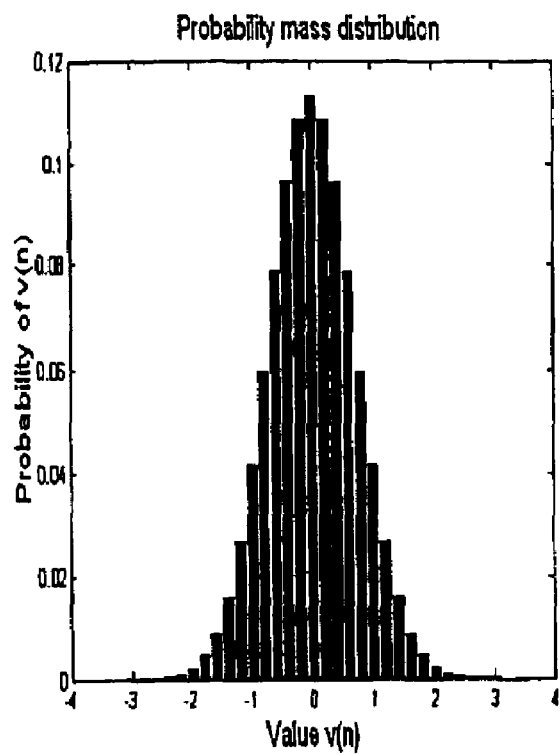
FIG. 3a is a graph of a probability mass distribution.
Figure 3B:
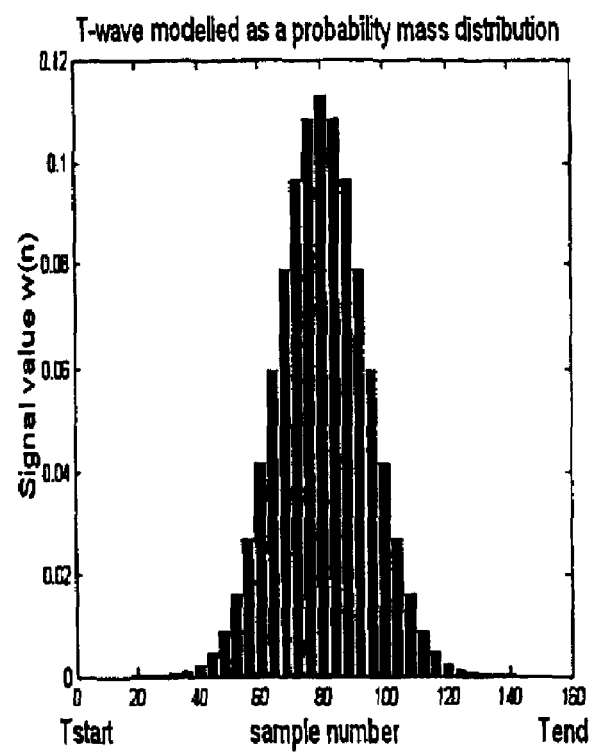
FIG. 3b shows a T-wave modelled as a probability mass distribution.

Parameters S1-S4 and F1-F8 is based on the calculation of modified skewness and kurtosis measures. Inspired by the summary measures of probability distributions used in the field of statistics the T-waves were modelled as probability mass distributions (FIGS. 3a, 3b) and assigned a centre (mean), width (standard deviation), an asymmetry measure and a convexity measure. Asymmetry and convexity calculations were then carried out based on the modified skewness and kurtosis measures ($3^{rd}$ and $4^{th}$ order moments) as follows:

The total area under the signal, m0, was calculated:

$$m_0 = \sum_{n=0}^{N-1} V[n]$$

The signal was normalized by the value of the area, m0:

$$w[n]=v[n]/m_0$$

Normalization facilitated the calculation of the moment functions, since w[n] shares a fundamental property with the probability mass function: A total area of 1. The $1^{st}$ order moment, m1, was calculated. m1 is the mean of the signal:

$$m_1 = \sum_{n=0}^{N-1} n*w[n]$$

The $2^{nd}$ order moment, m2, was calculated. m2 is the standard deviation of the signal:

$$m_2 = \left(\sum_{n=0}^{N-1} (n-m_1)^2 * w[n]\right)^{1/2}$$

FIG. 2 Isoelectric lines (dashed lines) in the signal are calculated from one P-Q interval to the following P-Q interval (Qstart—20 ms). The line values are subtracted from the corresponding ECG signal values giving the distances v(n). The result of this procedure is shown as an area plot with basis on the zero-line.

FIG. 3. a) Example probability mass distribution used when calculating standard skewness and kurtosis measures. b) Modified frequency distribution used in this study for calculating the modified skewness and kurtosis measures. Signal values v(n) are shown in FIG. 2.

4/8

Parameter Description

Symmetry
    S1 Skewness evaluated from Tstart to Tend.
    S2 Skewness evaluated from Tstart to Tend with Ttop as mean.
    S3 Skewness evaluated in a symmetric interval, 10% of the Tstart-Tend interval surrounding Ttop with Ttop as mean.
    S4 Skewness evaluated in a symmetric interval, 20% of the Tstart-Tend interval surrounding Ttop wit Ttop as mean.
    S5 Ratio of the tine interval from Tstart to Ttop and the time interval from Ttop to Tend.
    S6 Ratio of the average slope from Tstart to Ttop and from Ttop to Tend.

Flatness
    F1 Kurtosis evaluated from Tstart to Tend.
    F2 F1 normalized by the absolute Rtop-Qnadir value.
    F3 Kurtosis evaluated from Tstart to Tend with Ttop as mean.
    F4 F3 normalized by absolute Rtop-Qnadir value.
    F5 Kurtosis evaluated in a symmetric interval, 10% of the Tstart-Tend interval surrounding Ttop with Ttop as mean.
    F6 F5 normalized by absolute Rtop-Qnadir value.

F7 Kurtosis evaluated in a symmetric interval, 20% of the Tstart-Tend interval surrounding Ttop with Ttop as mean.

F8 Kurtosis normalized by the value of Rtop with Ttop as mean.

F9 Ratio of the total area under the T-wave from Tstart to Ttop and the corresponding time interval.

F10 F9 normalized by absolute Rtop-Qnadir value.

F11 Ratio of the total area under the T-wave from Ttop to Tend and the corresponding time interval.

F12 F11 normalized by absolute Rtop-Qnadir value.

F13 Ratio of the total area under the T-wave from Tstart to Tend and the corresponding time interval.

F14 F13 normalized by absolute Rtop-Qnadir value.

F15 Ratio of the height of Rtop and the width of the Tstart-Tend interval.

Duration

QTc The Q-T interval normalized by the square root of the R-R interval according to Bazett's formula.

D2 Time interval from Tstart to Tend.

D3 Time interval from Tstart to Ttop.

D4 Time interval from Ttop to Tend.

The table above shows a Complete list of the parameters used to characterize T-wave morphology. Parameters belong to one of three categories: symmetry, flatness and duration.

The $3^{rd}$ order moment, m3, was calculated. m3 is the modified skewness of the signal:

$$m_3 = \left( \sum_{n=0}^{N-1} (n-m_1)^3 * w[n] \right)^{1/3}$$

Finally the $4^{th}$ order moment, m4, was calculated. m4 is the modified kurtosis of the signal:

$$m_4 = \left( \sum_{n=0}^{N-1} (n-m_1)^4 * w[n] \right)^{1/4}$$

2.6 Data Analysis in Matlab

The T-wave morphology parameters for the acquired, pre-processed ECG recordings were evaluated using Matlab 6.0. Only valid data were analyzed—i.e. data from leads where the signal was not corrupted by high frequency noise and where the event detection algorithm was successful in detecting the relevant events with satisfactory precision. Parameter means and standard deviations were calculated for every T-wave in the signal on all leads. A great interlead variation in T-wave morphology may be an indicator of LQTS. Interlead variance was therefore examined by calculating the standard deviation of the lead means for each parameter.

Only the parameter means from lead V5 and interlead standard deviations were used as final parameter values. Hence, for every parameter in table 1, two parameters were calculated—one with index "meanV5" and one with index "std" e.g. F1meanV5 and F1std.

2.7 Statistical Analysis

In order to characterize and classify data from the three groups (KvLQT1, HERG and normal), the evaluated parameter values were processed using discriminant analysis. The analysis was carried out in SPSS version 11.5. The objective of the discriminant analysis was twofold: finding parameters that most efficiently discriminate between the groups and reducing the number of variables. Therefore a stepwise procedure was used with the Mahalanobis D2 as the most appropriate distance measure.

The entry/removal-criteria were adjusted in order to reduce the number of variables in the discriminant functions to achieve a 1:3 ratio between the number of variables and the population size (N=16). The criteria were empirically chosen to be pentry=0.045 and premoval=0.09 providing the desired 5 variables in the discriminant functions.

Figure 4:
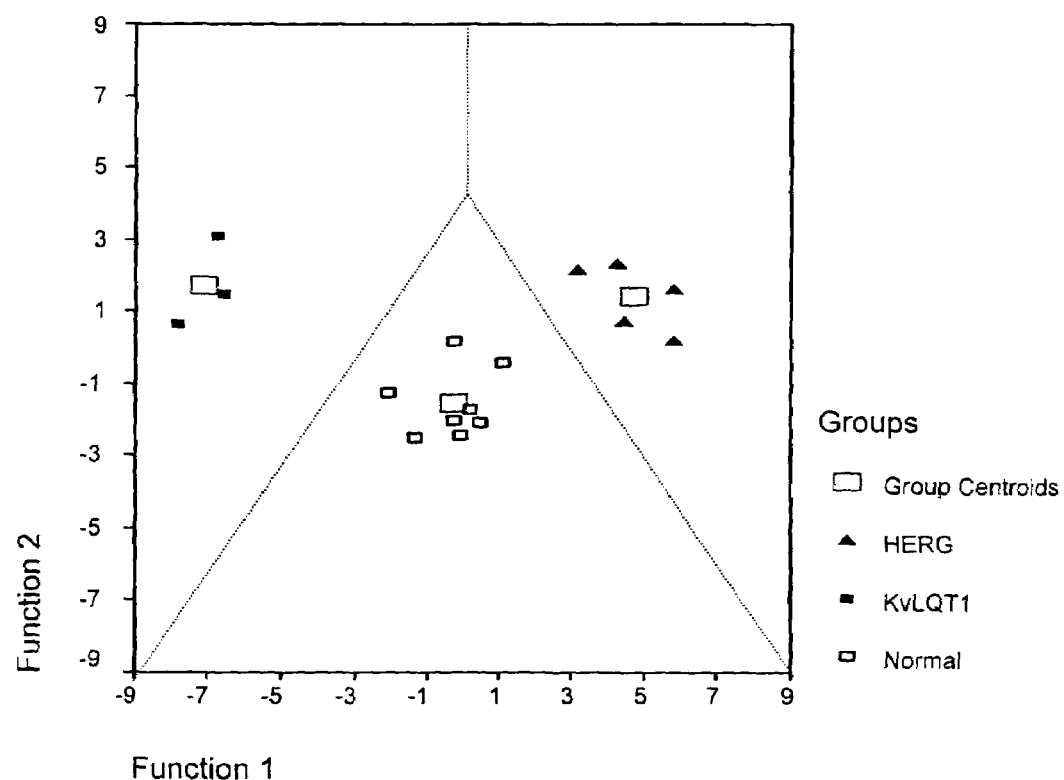
FIG. 4 is a scatterplot showing classification of individuals by genotype.
Figure 5A:
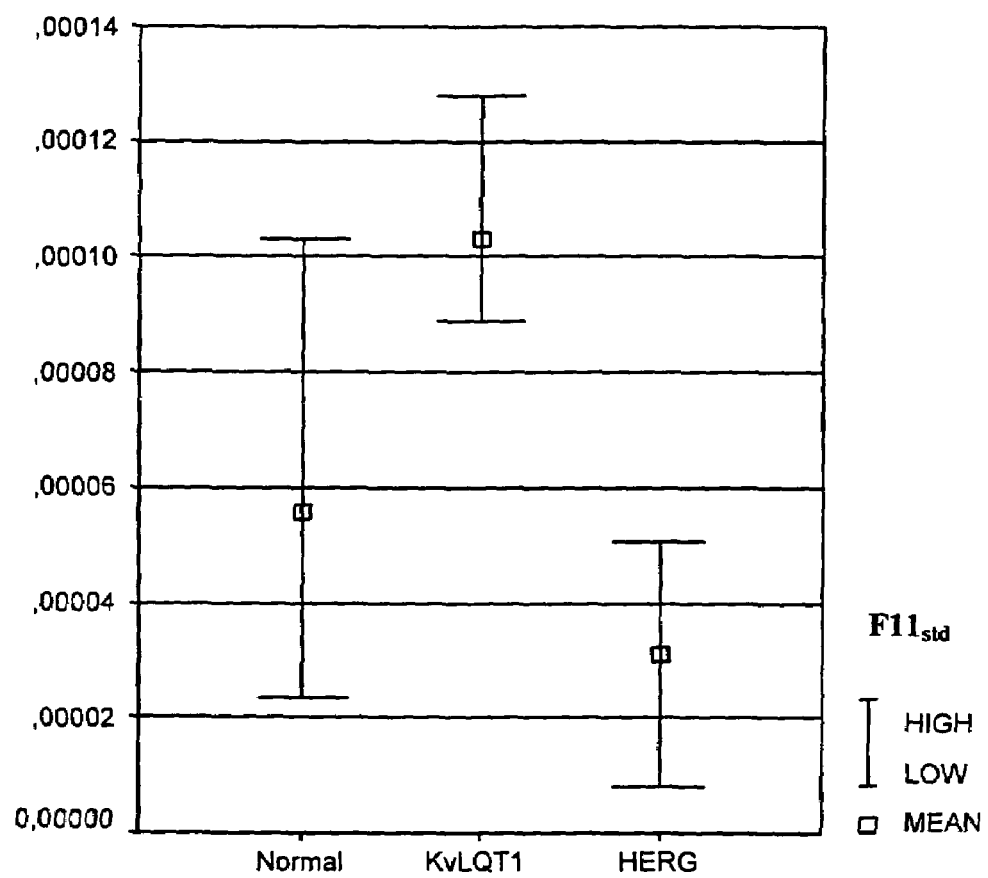
FIGS. 5a-5e reflect the analysis results of the parameters by the system.
Figure 5B:
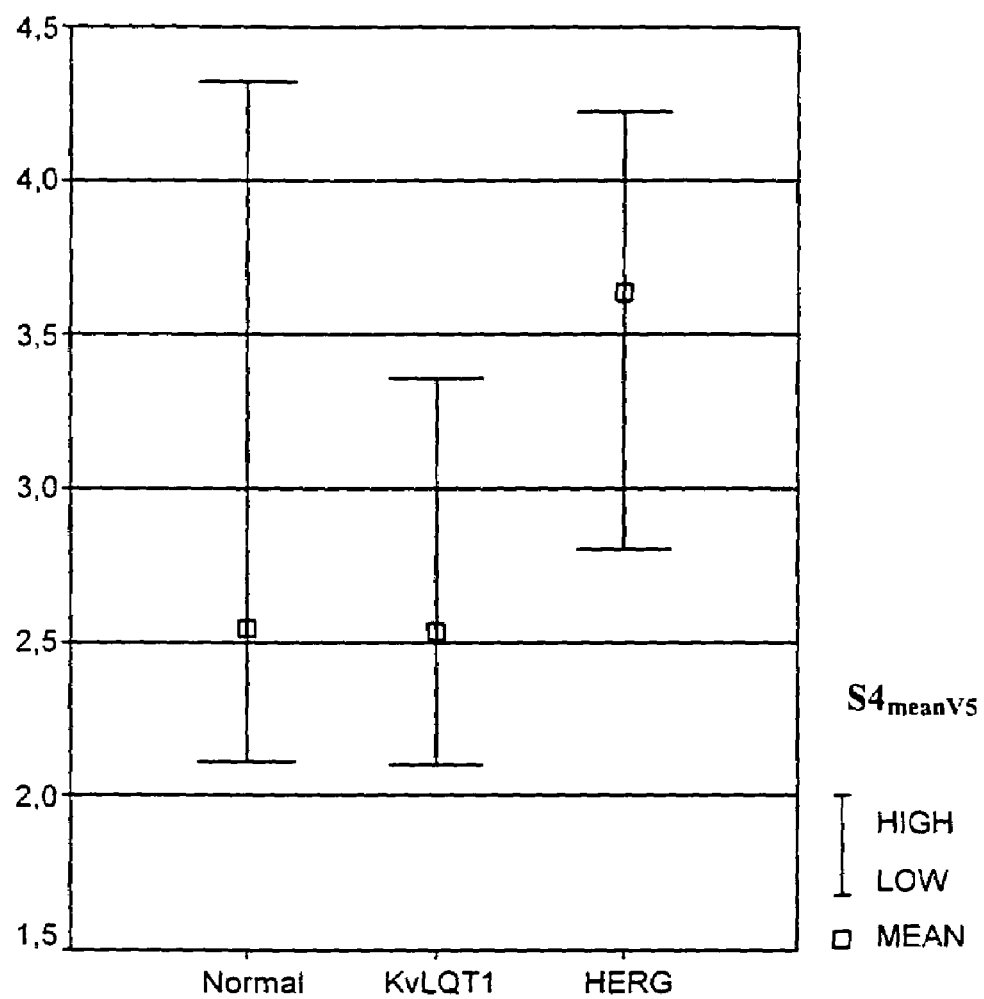
Figure 5C:
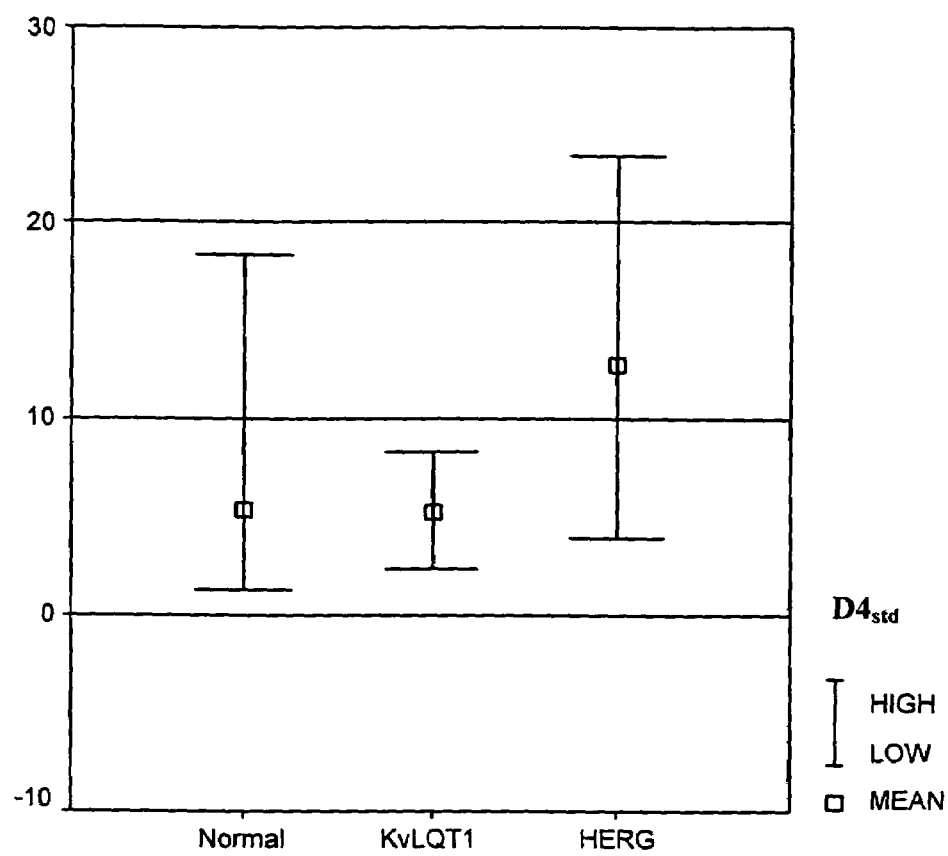
Figure 5D:
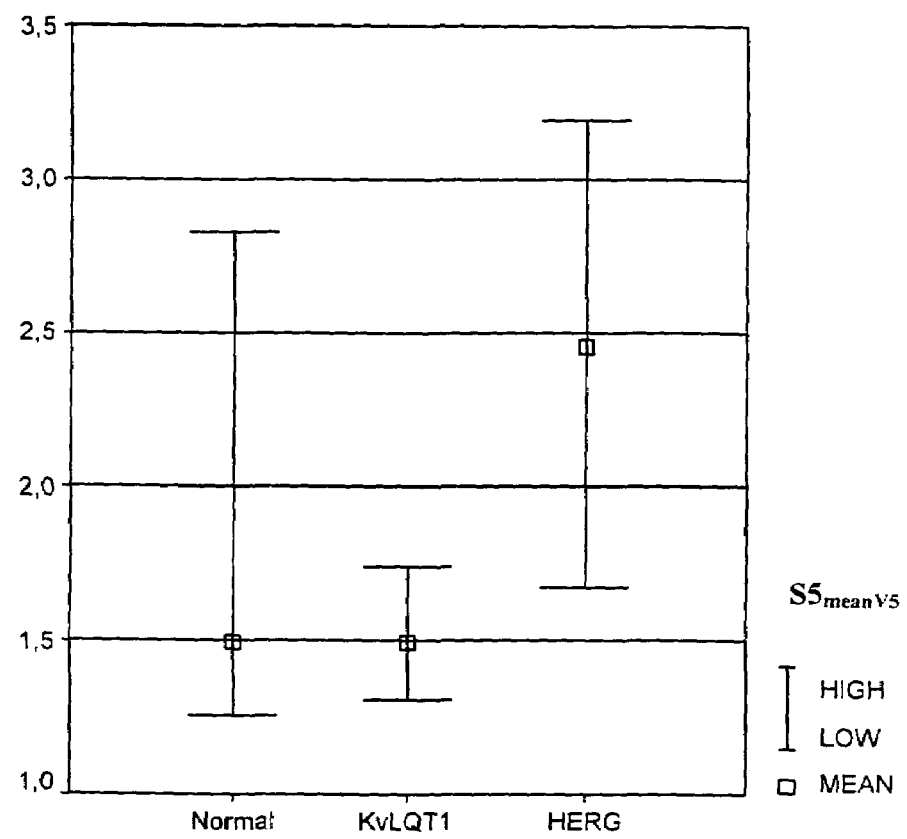
Figure 5E:
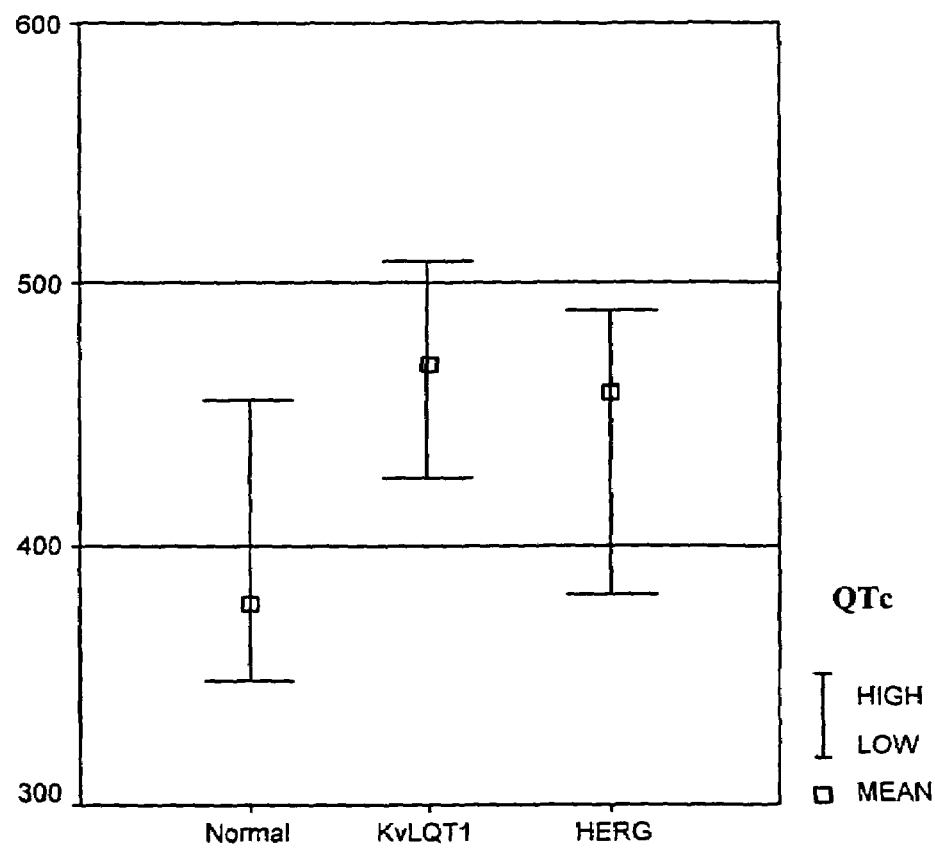

FIG. 4. Scatterplot showing classification of individuals by genotype. Separation of groups was carried out by 2 discriminant functions with 5 variables that characterize repolarisation by computation of symmetry, flatness and duration.

3. Results

The discriminant functions were based on data from all KvLQT1, HERG and normal subjects. The 5 parameters included in both discriminant functions are listed in table 2.

The discriminative efficiency of both generated functions was statistically significant after inclusion of all 5 parameters (function 1: $p<0.0001$, function 2: $p<0.005$).

Variables Entered

| Step | Entered |
|---|---|
| 1 | F11std |
| 2 | QTcmeanV5 |
| 3 | S5meanV5 |
| 4 | D4std |
| 5 | S4meanV5 |

Table 2. Variables used by the two discriminating functions. Stepwise introduction of more variables improved the ability of the functions to discriminate between KvLQT1, HERG and normal.

A scatterplot was generated from the discrimination functions and groupings of individual genotypes can be seen in FIG. 4. The dotted lines were read from the SPSS generated territorial map and manually added. The lines reflect borderlines where the differences between each pair of discrimination functions are zero. All 16 processed ECG's were correctly classified and showed at least one discriminatory characteristic as defined by the 5 parameters included in the discrimination functions. Cross validation of both discriminant functions was done with the leave-one-out method and all 16 subjects were again correctly grouped. Reducing the number of variables resulted in misclassified cases due to lack of one or more discriminatory characteristics. In light of this finding we elected to perform further analysis of the selected parameters in order to investigate the individual contributions of each variable to the separation of the three primary groups of subjects. Extreme values for all parameters were identified and the mean was computed.

The result is plotted in FIG. 5. As expected the extent of interlead flatness variation observed in HERG and normal individuals was lower than that found in KvLQT1 subjects. This is evidenced by the F11std parameter in FIG. 5a. When evaluating parameter values S4meanV5 and S5meanV5 (FIGS. 5b, d) the extent of 6/8 asymmetry in KvLQT1 and normal was generally less than that of HERG individuals. Both S4meanV5 and S5meanV5 are symmetry parameters and asymmetry in HERG individuals was augmented in two ways: When bifid T-waves were present the interval from Tstart to Ttop was prolonged due to the definition of Ttop used in this study (the last highest point on the T-wave). Also, when the initial portion before Ttop was prolonged in HERG individuals better discrimination was possible. Both phenomena were observed in HERG subjects. Generally the Bazett corrected QTc observed in HERG and KvLQT1 was higher than that of normal individuals (FIG. 5e). However overlap existed between all three groups preventing separation of the groups by QTc. Since no single parameter included in the discrimination functions was able to separate KvLQT1, HERG and normal, we proceeded to investigate the classification efficiency provided by the three primary categories represented by the parameters in the functions. This was carried out by generating new discrimination functions using parameters from one category only while excluding the other two. Then, from the new discrimination functions three additional functions were generated, this time allowing the inclusion of parameters from combinations of two categories. Scatterplots illustrating the results of this analysis are shown in FIGS. 6a-f. The first two functions (FIG. 6a) included parameters that characterize the symmetrical properties of the Twave. 83.1% of the 16 subjects were correctly classified. Arrows in FIG. 6a indicate the 3 misclassified subjects. A second discriminant analysis was performed using flatness parameters. This resulted in 93.8% correctly classified subjects. Only one subject was not correctly classified as indicated by the arrow on FIG. 6b. The misclassified case was the same HERG subject incorrectly classified using symmetry parameters. The discriminatory efficiency of duration parameters was also evaluated. Discrimination analysis resulted in 93.8% correctly classified subjects. One HERG subject was misclassified as KvLQT1. QTc was 416 ms and the subject showed relatively peaked T-waves similar to those found in KvLQT1. However the duration parameters failed to identify this morphological feature, thus reducing classification performance.

It can be noted that improved classification was obtained using flatness or duration parameters versus symmetry parameters and it seemed reasonable to investigate if further classification improvement could be achieved using a combination of several parameter categories.

FIG. 5. a) F11std—Interlead standard deviation of the ratio between the total area under the T-wave from Ttop to Tend and the corresponding time interval. b) S4meanV5—Lead V5 mean modified skewness evaluated in a symmetrical interval surrounding Ttop and corresponding to 20% of the interval between Tstart-Tend. c) D4std—Interlead standard deviation of the time interval from Ttop to Tend. d) S5meanV5—Lead V5 mean of the ratio between the time interval from Tstart to Ttop and the corresponding time interval from Ttop to Tend. e) Lead V5 mean QTc.

Figure 6A:
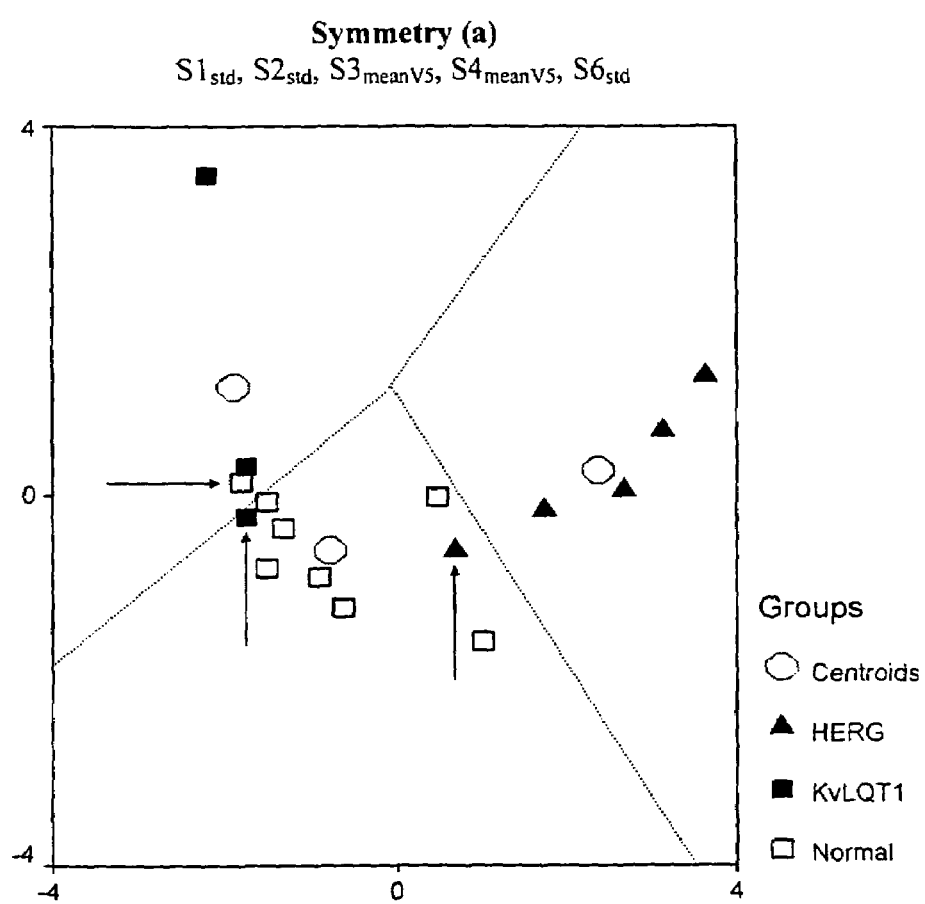
FIGS. 6a-6f show scatterplots illustrating the results of analysis by the system.
Figure 6B:
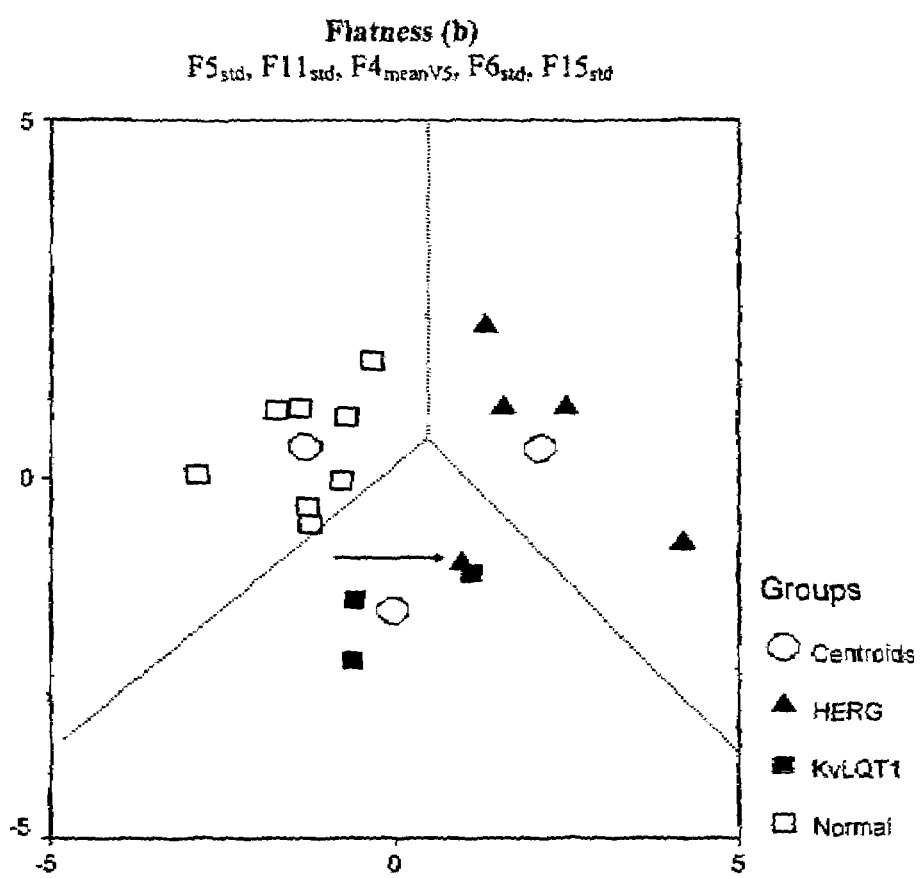
Figure 6C:
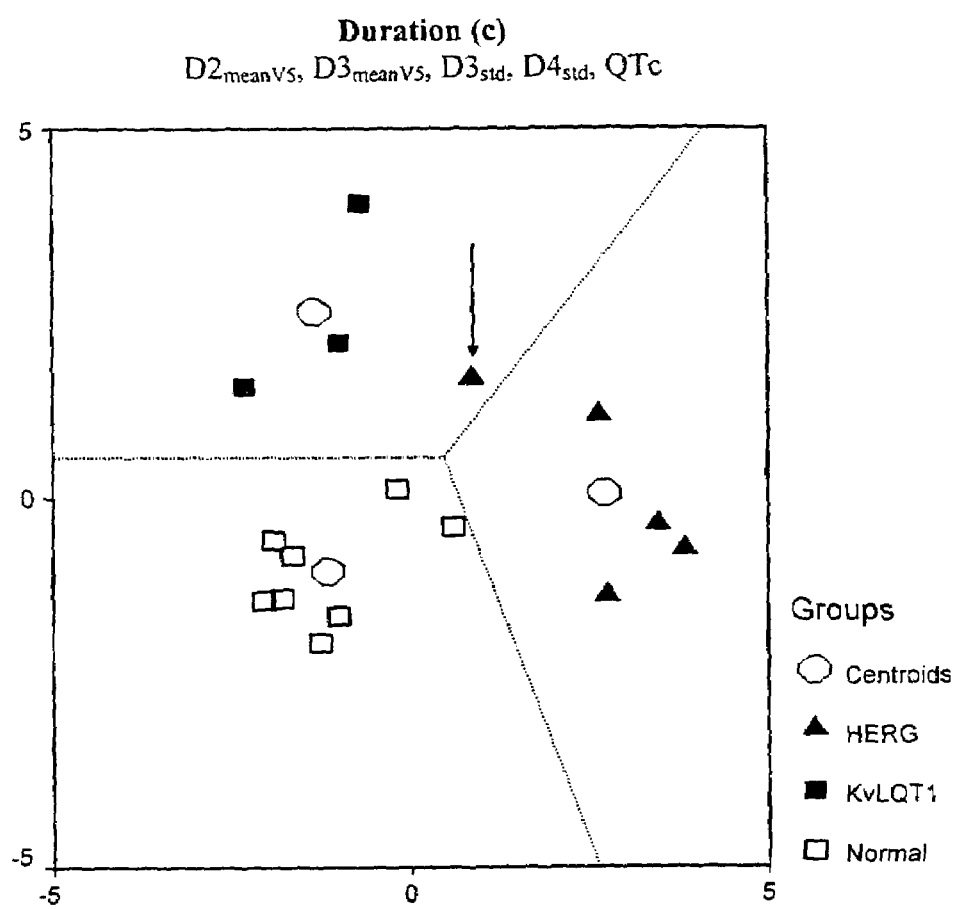
Figure 6D:
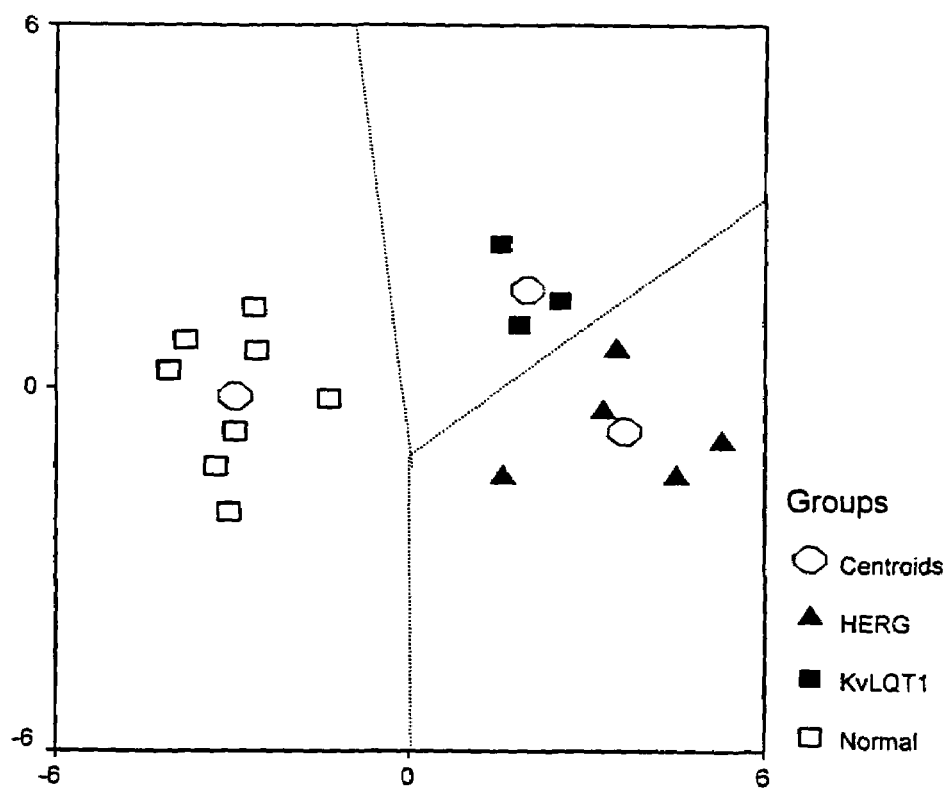
Figure 6E:
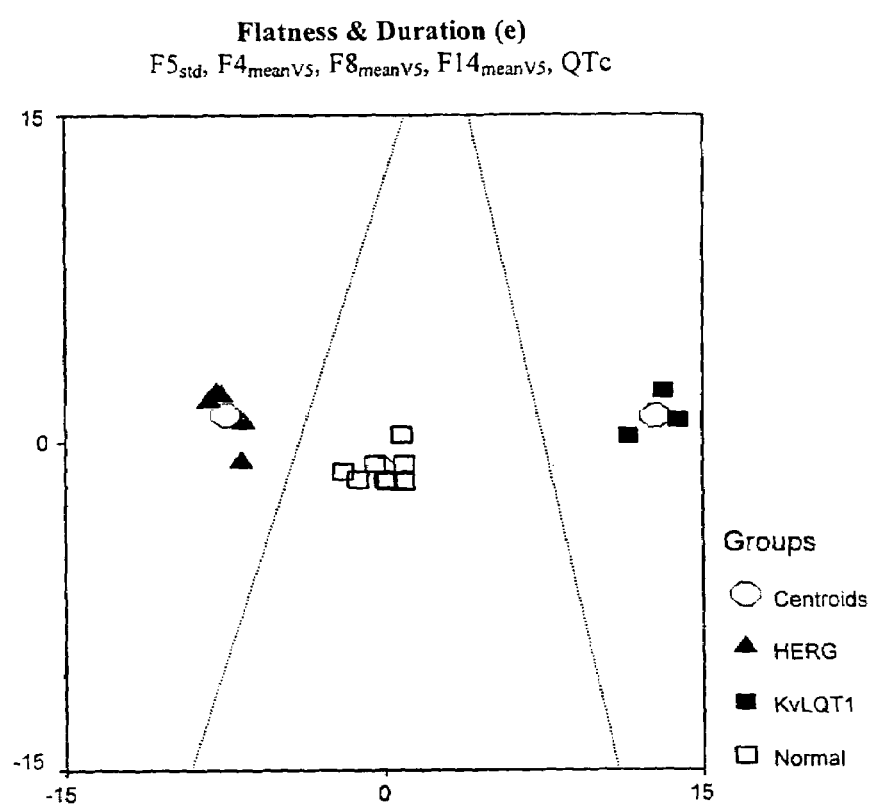
Figure 6F:
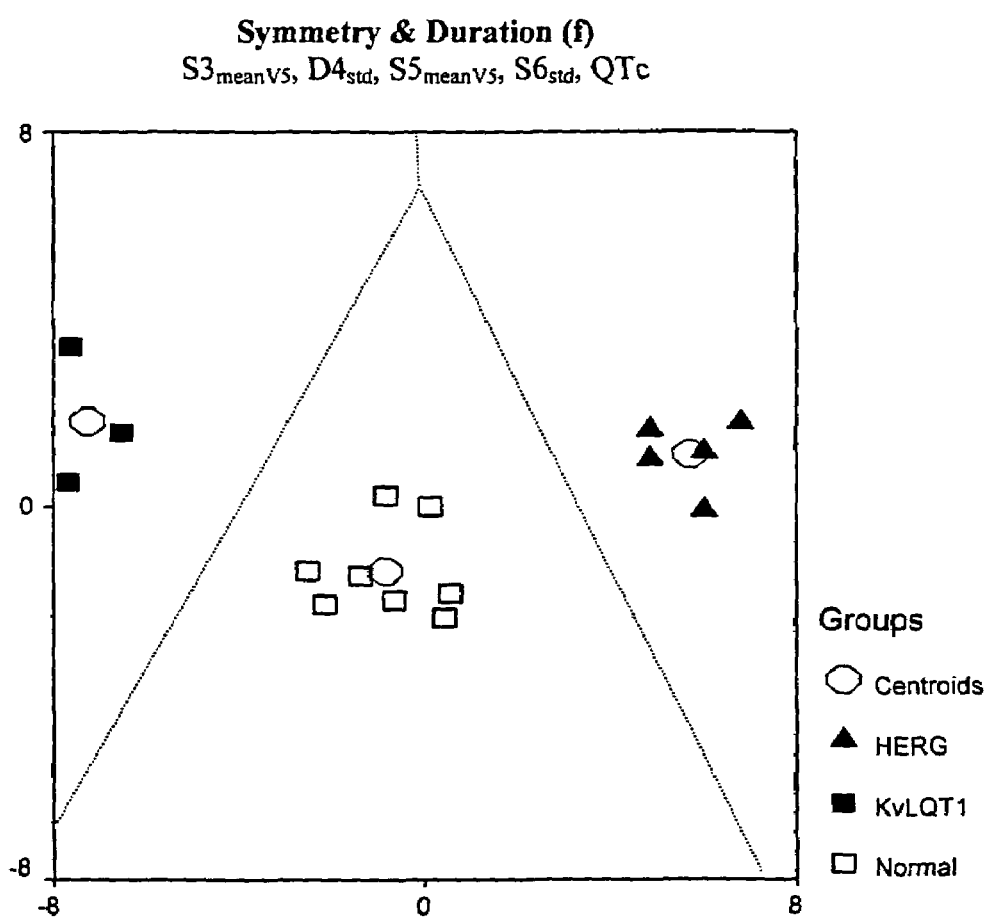

FIGS. 6d-f show the results of three separate discriminant analysis using combinations of parameters from two categories. It can be noted that classification of subjects was perfect in all cases, even when repolarisation duration was not considered (FIG. 6d).

4. Conclusion and Discussion

The initial discriminant analysis performed in this study resulted in perfect classification of all KvLQT1, HERG and normal subjects. In table 2 it was noted that the discriminant functions included parameters from all three categories; T-wave symmetry, T-wave flatness and duration. This is in agreement with the initial hypothesis that a combination of repolarisation duration and T-wave morphology characteristics could improve discrimination between KvLQT1, HERG and normal.

To understand why some subjects were misclassified using a reduced set of parameter categories (FIGS. 6a-c) the duration parameters and morphological characteristics of all 16 ECG's were examined.

Using only symmetry parameters, 3 subjects were misclassified. However no obvious visual characteristics on the three misclassified ECG's could be identified that explained the incorrect classifications. The Bazett corrected QTc was 347 ms for the normal subject, 425 ms KvLQT1, 476 ms HERG. Although an obviously prolonged QTc was present in the misclassified HERG subject it was not identified using symmetry parameters alone.

Discriminant analysis using parameters from the flatness category resulted in only 1 misclassification. Again no visual characteristics were identified to account for the misclassification. Although it was anticipated that the FIG. 6. a) The result of discriminant analysis using symmetry parameters resulted in three misclassified cases (arrows). Visual inspection of the ECG's revealed no apparent abnormalities to indicate the reason for incorrect misclassification. b) The result of discriminant analysis using flatness parameters. One incorrectly classified HERG subject was identified (arrow) even though no obvious visual abnormality indicated a different genotype. c) Result of discriminant analysis using duration parameters. This result illustrates the failure of duration parameters to discriminate between KvLQT1, HERG and normal (arrow). d-e) Combinations of parameters from two categories illustrate the improvement in classification efficiency when compared to FIGS. 6a-c evaluation of T-wave flatness would be able to discriminate HERG from KvLQT1 subjects this was not accomplished by using flatness as a single descriptor of repolarisation. Performing discriminant analysis based on the QTc parameter as the only variable resulted in 1 misclassification. This was not unexpected since it is well known that a substantial overlap in QTc values can exist between normal and affected individuals. The lack of unambiguous discrimination between all groups by use of the QTc parameter alone emphasizes the hypothesis that additional parameters are needed to classify LQTS individuals. By combining parameters from two categories it was found that the discriminatory strength was increased.

(FIGS. 6d-f) This was evidenced by the fact that no subjects were misclassified using two categories. A particularly interesting finding, was the perfect separation of all subjects that was obtained using symmetry and flatness parameters with no duration parameters included. This result implies the discriminatory strength inherent in parameters from those two categories. In addition it was found that symmetry or flatness parameters combined with duration parameters yielded perfect discrimination between all groups. Results from the discriminant analysis using one and two categories indicate that a combination of more parameter categories strengthen the overall discriminatory power of the classification functions. Combining these findings with the results from the three category discriminant analysis initially performed, it is reasonable to speculate that a substantially improved discrimination between KvLQT1, HERG and normal is possible using all three categories of parameters.

In light of the results obtained in this study we propose a new technique for discriminating between KvLQT1, HERG and normal subjects. Through multivariate discriminant analysis it was found that a combination of two duration parameters and three T-wave symmetry—and flatness parameters was sufficient to classify each of the 16 study subjects into one of the three distinct groups. Although no single parameter had the necessary discriminatory strength to classify the subjects, the combination of multiple parameters in two discrimination functions was statistically significant (function 1: $p<0.0001$, function 2: $p<0.005$). The encouraging results of multivariate repolarisation analysis found in this study support the use of symmetry—, flatness—and duration parameters to classify LQTS patients.

Further effort must be made to strengthen the statistical impact of this study and to investigate whether the proposed symmetry—, flatness—and duration parameters are the best suitable for the discrimination functions.

The use of the proposed multiple parameter categories to classify KvLQT1 and HERG genotypes may prove to be a powerful clinical tool in the making.

The invention will in the following be described in detail with reference to the drawing, where FIGS. 1 to 6 are mentioned in the text, and they are as such not further described.

Figure 7:
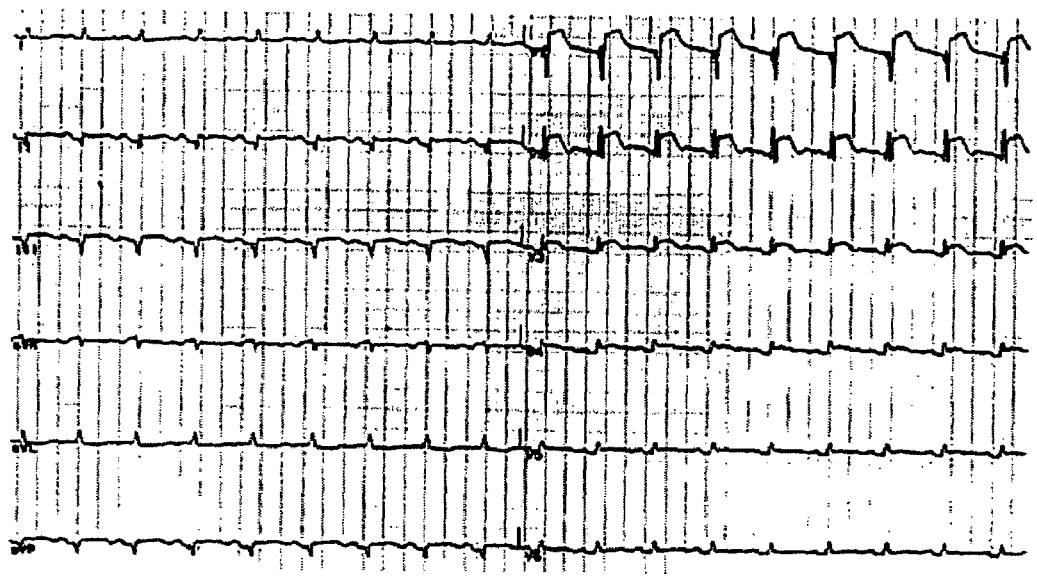
FIG. 7 shows examples of ECG-curvature having ST-elevation myocardial infarction.

FIG. 7 shows examples of ECG-curvature having ST-elevation myocardial infarction, where the active parameters for indicating ST-elevation myocardial infarction is ST-elevation, ST-morphology, T-wave morphology and Q-wave morphology.

Figure 8:
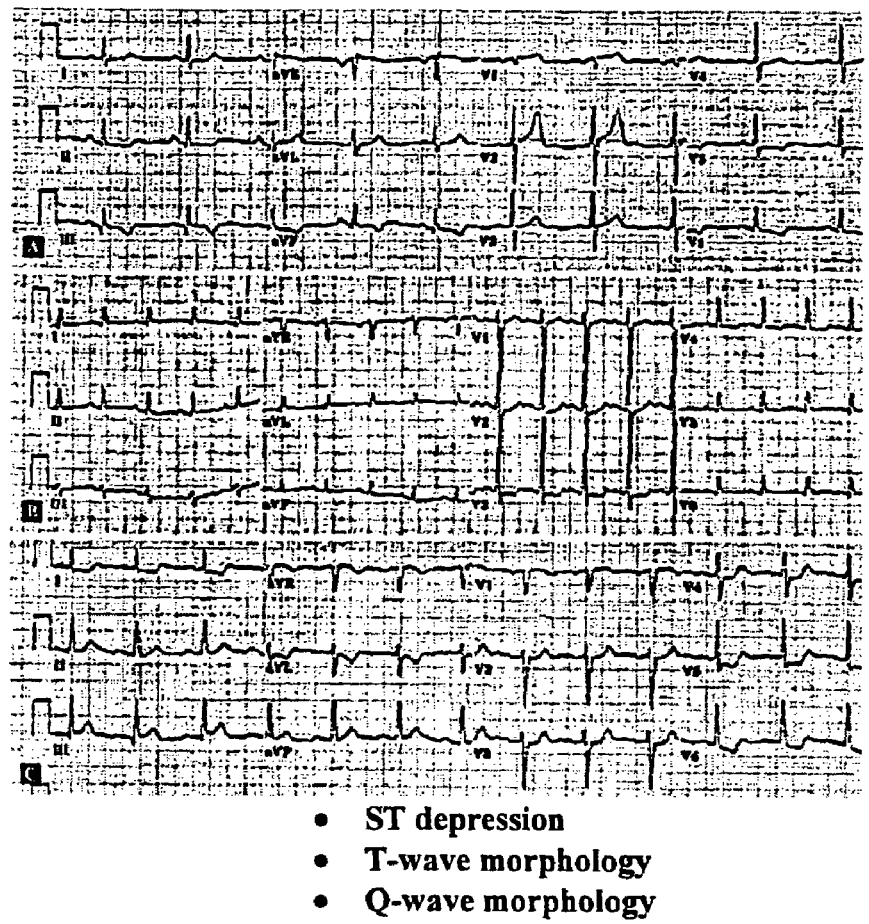
FIG. 8 shows curvaturic non ST-elevation myocardial infarction.

FIG. 8 shows curvaturic non ST-elevation myocardial infarction, where parameters of ST depression, T-wave morphology or Q-wave morphology could be used.

Figure 9:
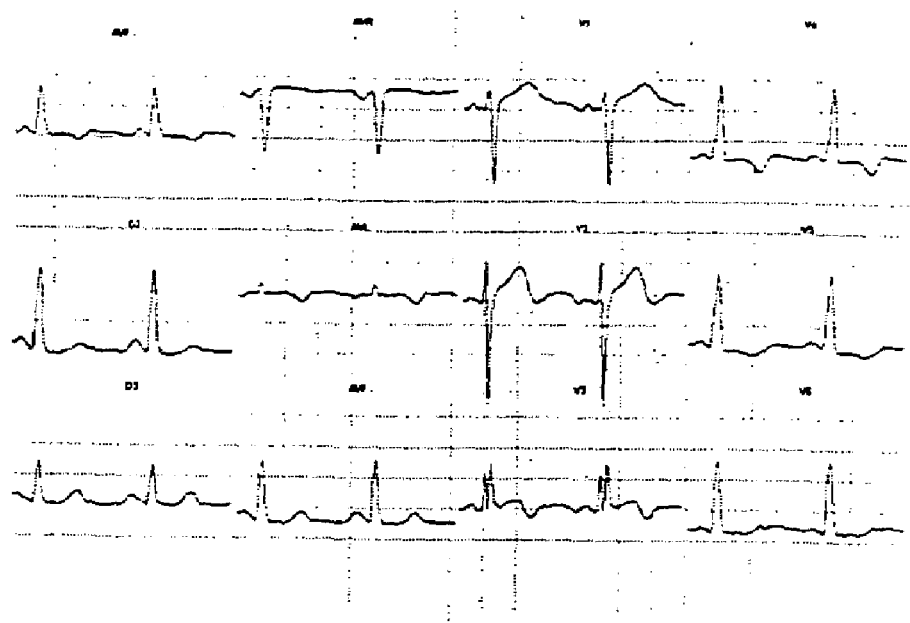
FIG. 9 shows a ECG-curvature indicating Cardiomyopathia.

FIG. 9 shows a ECG-curvature indicating Cardiomyopathia where the following parameters can be used for indication: P-wave morphology, QRS duration, S-wave morphology and T-wave morphology.

Figure 10:
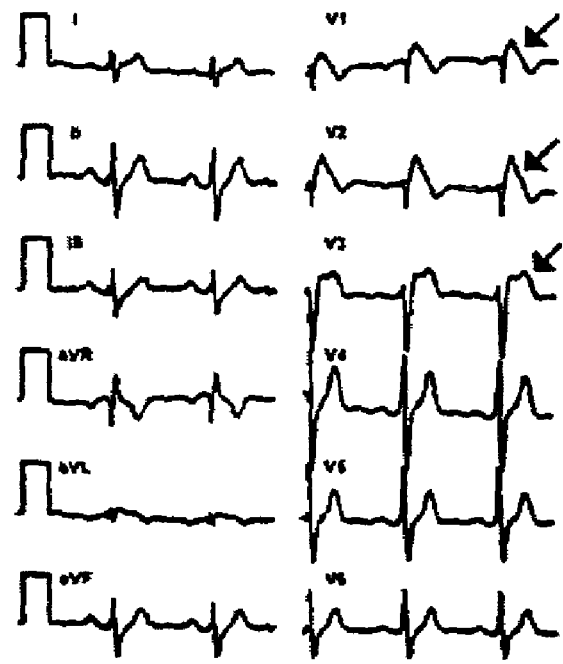
FIG. 10 shows curvatures indicating Brugada Syndrome.

FIG. 10 shows in the same way indications for Brugada Syndrome. Here, the effective parameters for indication are PR-duration, ST-elevation, ST morphology and T-wave morphology.

Figure 11:
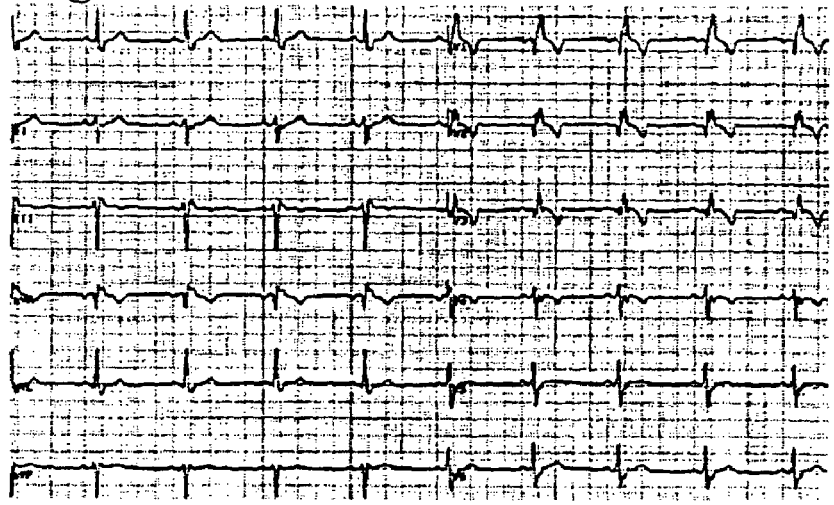
FIG. 11 shows curvatures referring to Right bundle branch block.

FIG. 11 shows curvatures referring to Right bundle branch block RBBB where the parameters could be QRS duration, R-wave morphology, T-wave morphology and ST-elevation.

Figure 12:
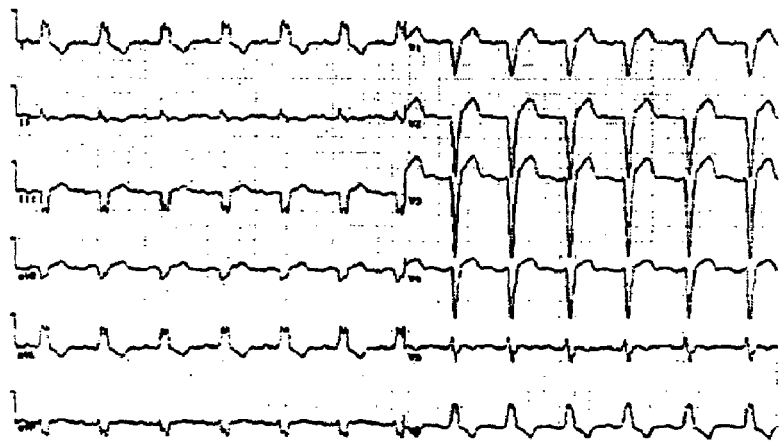
FIG. 12 shows curvatures indicating Left bundle branch block.

FIG. 12 shows curvatures indicating Left bundle branch block LBBB where the effective parameters could be QRS duration, R-wave morphology and T-wave morphology.

Figure 13:
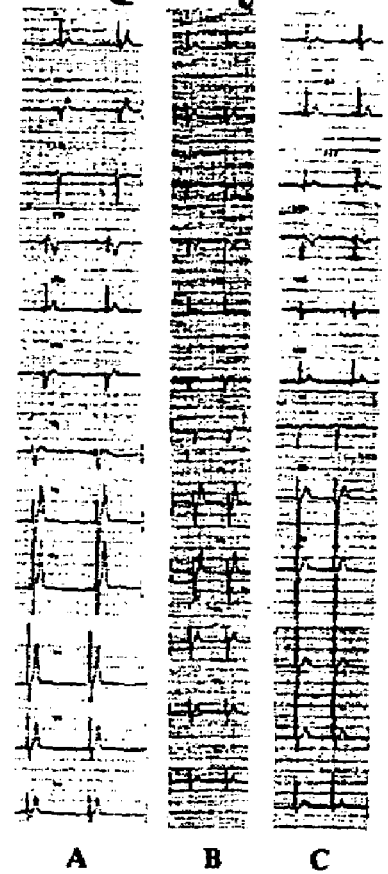
FIG. 13 shows curvatures indicating Short QT syndrome.

FIG. 13 shows curvatures indicating Short QT syndrome where parameters for indication could be Q-T duration and T-wave morphology.

Figure 14:
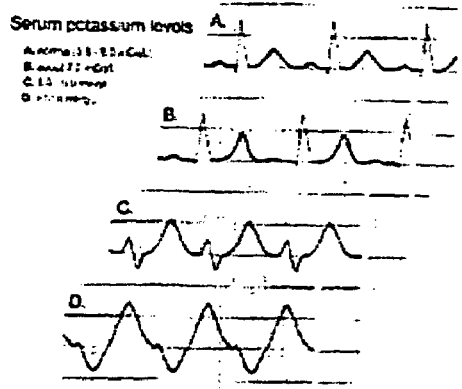
FIG. 14 shows curvatures indicating Hyperkalemia.

FIG. 14 shows curvatures indicating Hyperkalemia where parameters effective for indications are P-wave morphology, T-wave morphology, QRS duration, QT duration and PR duration.

Figure 15:
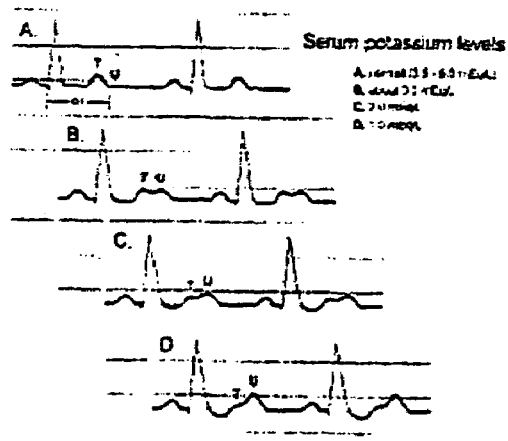
FIG. 15 shows curvatures indicating Hypokalemia.

FIG. 15 shows curvatures indicating Hypokalemia where the effective parameters for indication seem to be QT duration, T-wave morphology and ST depression.

Figure 16:
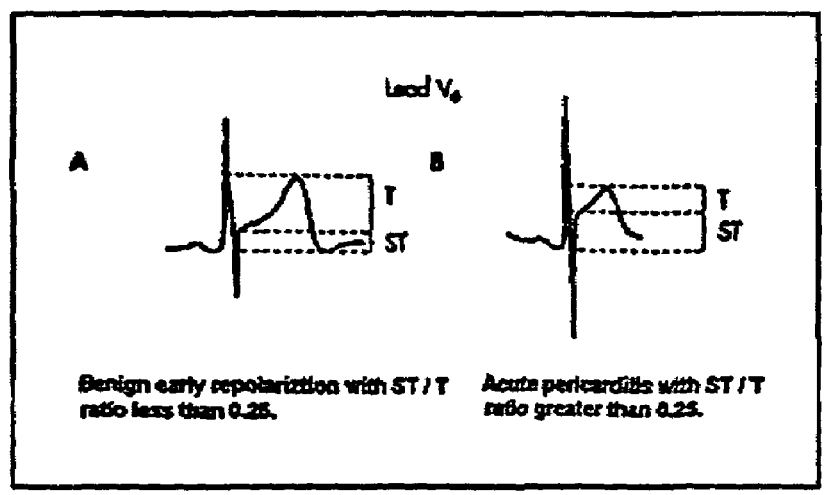
FIG. 16 shows curvatures indicating Pericarditis.

FIG. 16 shows curvatures indicating Pericarditis where the effective parameters are ST elevation, ST morphology, Q-wave morphology and PR depression.

Figure 17:
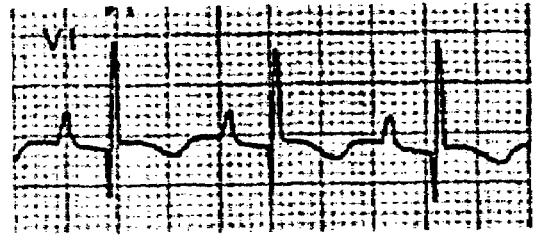
FIG. 17 shows a curvature indicating Right Ventricular Hypertrophy (RVH).

FIG. 17 shows a curvature indicating Right Ventricular Hypertrophy (RVH) where the effective parameters for indication are Q-wave morphology, QRS duration, S-wave morphology and T-wave morphology.

Figure 18:
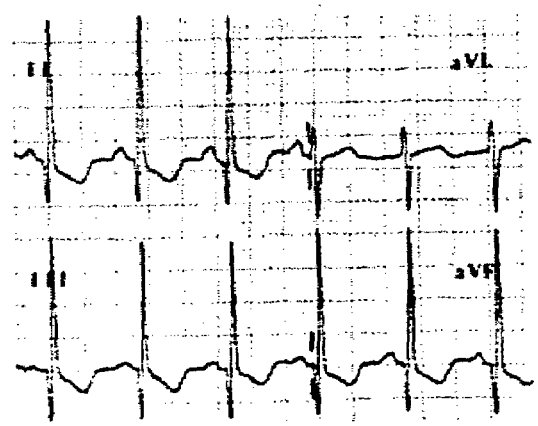
FIG. 18 shows curvatures indicating Left Ventricular Hypertrophy (LVH).

FIG. 18 shows curvatures indicating Left Ventricular Hypertrophy (LVH) where the effective parameters for indication are Q-wave morphology, QRS duration, S-wave morphology and T-wave morphology.

Figure 19:
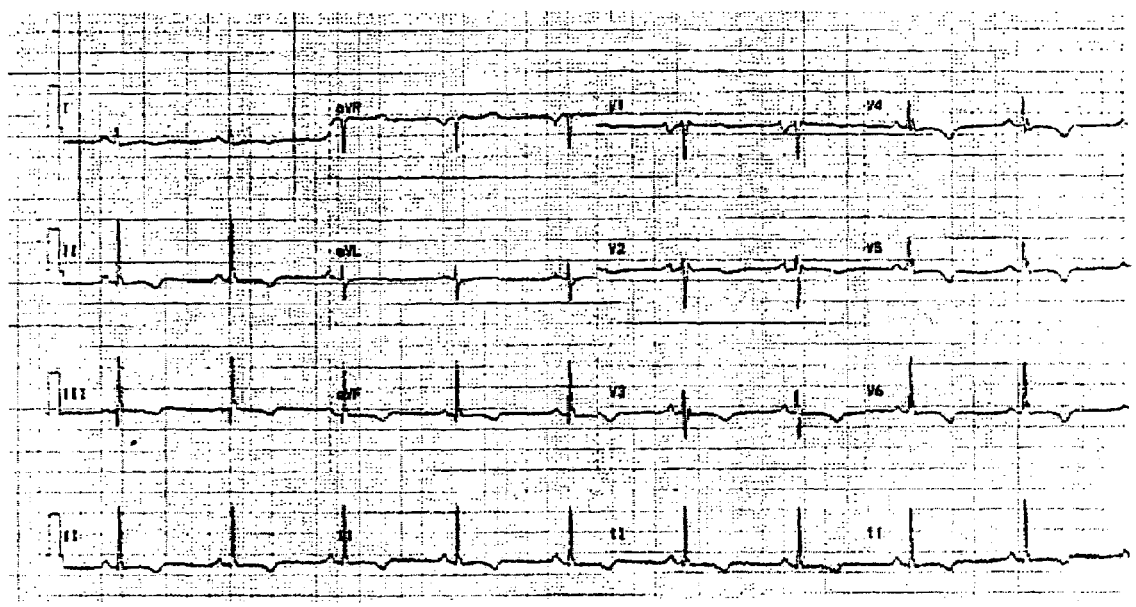
FIG. 19 shows curvatures indicating Arrhythmogenic Right Ventricular Dysplasia.
Figure 20A:
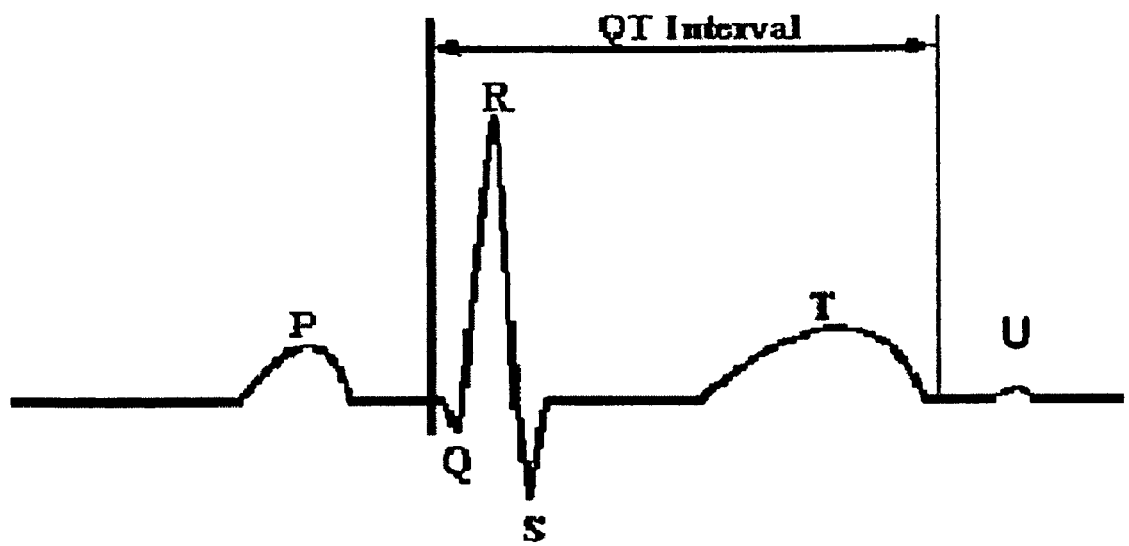
FIGS. 20a and 20b show parameters on typical ECG curvatures.
Figure 20B:
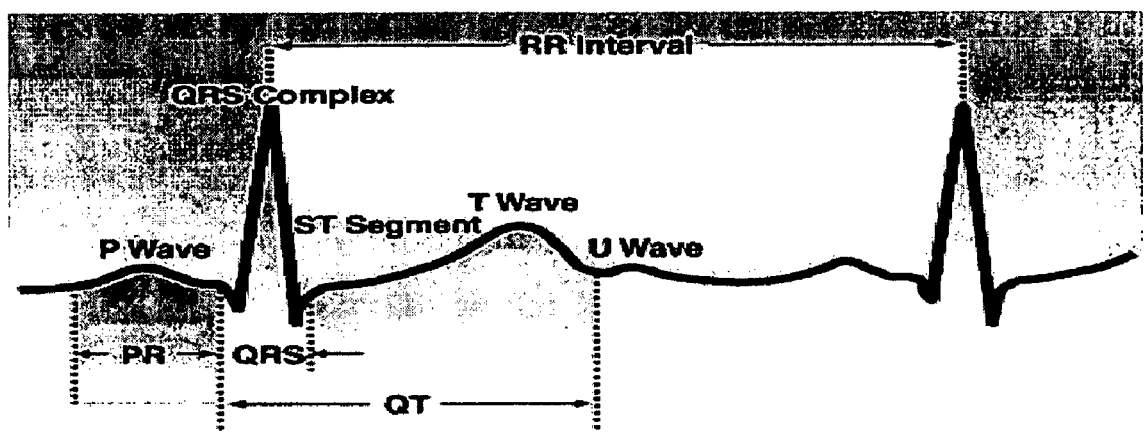

FIG. 19 shows curvatures indicating Arrhythmogenic Right Ventricular Dysplasia where the parameters are QRS duration, S-wave morphology and T-wave morphology is used.

While the invention has been described with reference to specific embodiments, modifications and variations of the invention may be constructed without departing from the scope of the invention, which is defined by the following claims.

We claim:

1. Method for analysing ECG curvature, which curvature contains a number of parameters, wherein the method for analysing the ECG curvature incorporates the steps of:

a) receiving ECG curvature from a source,
b) indicating a number of different parameters contained in the received ECG curvature,
c) storing the parameters in storage means,
d) select disease specific parameters in the storage means
e) combine selected parameters in mathematical analysing means
f) represent the result of the mathematical analysis as a point in a coordinate system, comprising at least two axes,
g) compare the actual placement in the coordinate system with a number of reference parameters stored in a memory,
h) indicating diseases having influence on the ECG curvature.

2. Method according to claim 1, wherein the method repeats the analysing process for further selected parameters for indicating further diseases.

3. Method according to claim 2, wherein the method divides parameters into at least three groups, which groups contains parameters selected from the group consisting of symmetry, flatness, duration, and combinations thereof.

4. A system for analyzing ECG curvatures and isolating at least one among a number of different parameters, each of which relates to a section of ECG curvature, comprising an ECG source, an input device connected to the ECG source, indicator reflecting different parameters of a received ECG curvature and indicating potential symptoms relative to diseases responsive to the different parameters and based on the diseases influencing the ECG curvature, a computer readable medium encoded with a program for carrying out a first mathematical analysis for combining a first number of selected parameters, outputting a result of the first mathematical analysis as a representative point in a coordinate system, the coordinate system comprising at least two axes, comparing actual placement in the coordinate system with a number of reference parameters stored in the system, and indicating symptoms of diseases having influence on the ECG curvature.

5. System of claim 4, further comprising repeating the analyzing process in the system for further selected parameters and indicating further possible diseases or symptoms.

6. System of claim 5, wherein the parameters are divided into at least two main groups in the system.

7. System of claim 6, wherein the parameters are selected from the group consisting of symmetry, flatness, duration, and combinations thereof.

8. System of claim 7, wherein the group of symmetry comprises parameters selected from the group consisting of the following parameters and combinations thereof:

S1 Skewness evaluated from Tstart to Tend,
S2 Skewness evaluated from Tstart to Tend with Ttop as mean,
S3 Skewness evaluated in a symmetric interval, 10% of the Tstart-Tend interval surrounding Ttop with Ttop as mean
S4 Skewness evaluated i a symmetric interval, 20% of the Tstart-Tend interval surrounding Ttop wit Ttop as mean,
S5 Ratio of the time interval from Tstart to Ttop and the time interval from Ttop to Tend,
S6 Ratio of the average slope from Tstart to Ttop and from Ttop to Tend, wherein the group of flatness is selected form the group consisting of the following parameters and combinations thereof:
F1 Kurtosis evaluated from Tstart to Tend,
F2 F1 normalized by the absolute Rtop-Qnadir value, F3 Kurtosis evaluated from Tstart to Tend with Ttop as mean,
F4 F3 normalized by absolute Rtop-Qnadir value,
F5 Kurtosis evaluated in a symmetric interval, 10% of the Tstart-Tend interval surrounding Ttop with Ttop as mean,
F6 F5 normalized by absolute Rtop-Qnadir value,
F7 Kurtosis evaluated in a symmetric interval, 20% of the Tstart-Tend interval surrounding Ttop with Ttop as mean,
F8 Kurtosis normalized by the value of Rtop with Ttop as mean,
F9 Ratio of the total area under the T-wave from Tstart to Ttop and the corresponding time interval,
F10 F9 normalized by absolute Rtop-Qnadir value,
F11 Ratio of the total area under the T-wave from Ttop to Tend and the corresponding time interval,
F12 F11 normalized by absolute Rtop-Qnadir value
F13 Ratio of the total area under the T-wave from Tstart to Tend and the corresponding time interval,
F14 F13 normalized by absolute Rtop-Qnadir value,
F15 Ratio of the height of Rtop and the width of the Tstart-Tend interval, wherein the group of duration is selected from the group consisting of the following parameters and combinations thereof:
QTc The Q-T interval normalized by the square root of the R-R interval according to Bazett's formula,
D2 Time interval from Tstart to Tend,
D3 Time interval from Tstart to Ttop,
D4 Time interval from Ttop to Tend.

9. System according to claim 6, further comprising combining parameters from different groups.

10. System according to claim 7, further comprising a computer readable medium encoded with a program for carrying out system analysis of the QT interval of the ECG curvature for indicating Long QT syndrome.

11. A system for analysing ECG curvature wherein at least one among a number of different parameters is isolated, which system has input means connected to an ECG source and a processor configured to indicate and/or isolate parameters, combine them in a mathematical analysis, and compare the results of the mathematical analysis with reference parameters, where the different parameters of a received ECG curvature are indicated and/or isolated for indicating possible symptoms which relates to or are indications of certain diseases, where said diseases are known to influence the ECG curvature, and that a first number of selected parameters, are combined in at least a first mathematical analysis, where the result of the analysis is represented as a point in a coordinate system, comprising at least two axes, where the system compares the actual placement in the coordinate system with a number of reference parameters stored in the system, for indicating symptoms of diseases having influence on the ECG curvature, wherein the mathematical analysis is repeated in the system for further selected parameters for indicating further possible diseases or symptoms, wherein the parameters are divided into at least two main groups in the system, which groups contains parameters of symmetry, flatness and duration.

12. System according to claim 11, wherein the group of symmetry contains at least following parameters:
S1 Skewness evaluated from Tstart to Tend,
S2 Skewness evaluated from Tstart to Tend with Ttop as mean,
S3 Skewness evaluated in a symmetric interval, 10% of the Tstart-Tend interval surrounding Ttop with Ttop as mean
S4 Skewness evaluated i a symmetric interval, 20% of the Tstart-Tend interval surrounding Ttop wit Ttop as mean,
S5 Ratio of the time interval from Tstart to Ttop and the time interval from Ttop to Tend,
S6 Ratio of the average slope from Tstart to Ttop and from Ttop to Tend, where the group of flatness contains at least the following parameters:
F1 Kurtosis evaluated from Tstart to Tend,
F2 F1 normalized by the absolute Rtop-Qnadir value,
F3 Kurtosis evaluated from Tstart to Tend with Ttop as mean,
F4 F3 normalized by absolute Rtop-Qnadir value,
F5 Kurtosis evaluated in a symmetric interval, 10% of the Tstart-Tend interval surrounding Ttop with Ttop as mean,
F6 F5 normalized by absolute Rtop-Qnadir value,
F7 Kurtosis evaluated in a symmetric interval, 20% of the Tstart-Tend interval surrounding Ttop with Ttop as mean,
F8 Kurtosis normalized by the value of Rtop with Ttop as mean,
F9 Ratio of the total area under the T-wave from Tstart to Ttop and the corresponding time interval,
F10 F9 normalized by absolute Rtop-Qnadir value,
F11 Ratio of the total area under the T-wave from Ttop to Tend and the corresponding time interval,
F12 F11 normalized by absolute Rtop-Qnadir value
F13 Ratio of the total area under the T-wave from Tstart to Tend and the corresponding time interval,
F14 F13 normalized by absolute Rtop-Qnadir value,
F15 Ratio of the height of Rtop and the width of the Tstart-Tend interval, where the group of duration contains at least the following parameters:
QTc The Q-T interval normalized by the square root of the R-R interval according to Bazett's formula,
D2 Time interval from Tstart to Tend,
D3 Time interval from Tstart to Ttop,
D4 Time interval from Ttop to Tend.

13. System according to claim 11, wherein the system is combining parameters from different groups.

14. System according to claim 12, wherein the system analyses the QT interval of the ECG curvature for indicating Long QT syndrome.

15. A system for analysing ECG curvature wherein at least one among a number of different parameters, each of which relates to a section of ECG curvature, is isolated, which system has input means connected to an ECG source and a processor configured to indicate and/or isolate parameters, combine them in a mathematical analysis, and compare the results of the mathematical analysis with reference parameters, where the different parameters of a received ECG curvature are indicated and/or isolated for indicating possible symptoms which relates to or are indications of certain diseases, where said diseases are known to influence the ECG curvature, and that a first number of selected parameters, are combined in at least a first mathematical analysis, where the result of the analysis is represented as a point in a coordinate system, comprising at least two axes, where the system compares the actual placement in the coordinate system with a number of reference parameters stored in the system, for indicating symptoms of diseases having influence on the ECG curvature.

16. System according to claim 15, wherein the mathematical analysis is repeated in the system for further selected parameters for indicating further possible diseases or symptoms.

* * * * *